United States Patent
Carrott et al.

(10) Patent No.: US 6,909,792 B1
(45) Date of Patent: **\*Jun. 21, 2005**

(54) HISTORICAL COMPARISON OF BREAST TISSUE BY IMAGE PROCESSING

(75) Inventors: David T. Carrott, Bristow, VA (US); Thomas M. Burke, Bothell, WA (US)

(73) Assignee: Litton Systems, Inc., Agoura Hills, CA (US)

( * ) Notice: Subject to any disclaimer, the term of this patent is extended or adjusted under 35 U.S.C. 154(b) by 611 days.

This patent is subject to a terminal disclaimer.

(21) Appl. No.: 09/602,251

(22) Filed: Jun. 23, 2000

(51) Int. Cl.[7] .............................. G06K 9/00; G06K 9/32
(52) U.S. Cl. ....................... 382/128; 382/129; 382/130; 382/131; 382/132; 382/294
(58) Field of Search ............................... 382/128–132, 382/294

(56) References Cited

U.S. PATENT DOCUMENTS

| | | | | |
|---|---|---|---|---|
| 5,042,077 A | | 8/1991 | Burke | 382/51 |
| 5,433,202 A | * | 7/1995 | Mitchell et al. | 600/444 |
| 5,491,627 A | | 2/1996 | Zhang et al. | 364/413.2 |
| 5,627,907 A | * | 5/1997 | Gur et al. | 382/132 |
| 5,644,649 A | | 7/1997 | Schoeters et al. | 382/132 |
| 5,784,431 A | * | 7/1998 | Kalend et al. | 378/65 |
| 5,982,953 A | * | 11/1999 | Yanagita et al. | 382/294 |
| 6,285,787 B1 | * | 9/2001 | Kawachi et al. | 382/209 |
| 6,310,477 B1 | * | 10/2001 | Schneider | 324/307 |
| 6,351,660 B1 | * | 2/2002 | Burke et al. | 600/425 |
| 6,363,163 B1 | * | 3/2002 | Xu et al. | 382/130 |
| 6,453,058 B1 | * | 9/2002 | Murthy et al. | 382/128 |
| 6,477,262 B2 | * | 11/2002 | Wang | 382/132 |
| 6,484,047 B1 | * | 11/2002 | Vilsmeier | 600/407 |
| 6,538,791 B2 | * | 3/2003 | Trezza | 359/237 |

* cited by examiner

Primary Examiner—Andrew W. Johns
Assistant Examiner—Hussein Akhavannik
(74) Attorney, Agent, or Firm—Koppel, Jacobs, Patrick & Heybl (57) ABSTRACT

An image processing system and method visually documents and displays changes between historical and later mammographic images, preferably in three dimensions. A composite image is created which visually emphasizes temporal differences between the historical and later images. Preferably three-dimensional, digitized images, displayable in various projections, are stored for archival purposes on computer readable media. An image processor preferably exploits an optical correlator to register the historical and later images accurately and provide correlation values as temporal scalars of the differences. The registered images are then compared, voxel-by-voxel, to detect temporal differences. The composite image is displayed with synthetic colors or other visual clues to emphasize apparent changes (for example, tumor growth or shrinkage).

14 Claims, 10 Drawing Sheets

HISTORICAL COMPARISON OF BREAST TISSUE BY IMAGE PROCESSING

BACKGROUND OF THE INVENTION

1. Field of the Invention

The invention relates generally to ultrasonic and radiographic medical imaging, and particularly to three-dimensional, ultrasonic mammography for the purpose of detecting and visualizing breast lesions.

2. Description of the Related Art

The standard of care for managing breast disease includes (in order) detection, diagnostic work-up, definitive diagnosis, treatment, adjuvant therapy and follow-up. In a large number of cases, the health care provider will not consider a biopsy justified and rather will opt to follow the situation with examinations every three to six months. In other cases the health care provider will typically also want to follow the progress of the lesion after adjuvant therapies are administered. This implies repeated imaging of the region of tissue containing the lesion and comparison of the earlier and later images, to detect and characterize any changes in the lesion.

Various imaging modalities are available to visualize lesions, including X-ray (most common), ultrasonography, magnetic resonance imaging and other known methods. Whatever imaging method is used, to make meaningful before/after comparisons it is necessary to insure that the same region of tissue is under examination. Preferably the tissue should be projected from the same viewing angle in both before and after images. Comparison and even interpretation of images is complicated in part because the region of interest is a three-dimensional volume, while the image is a projection onto a two-dimensional plane or planes. Three dimensional positions and relationships must be inferred or calculated, based upon the available projections. Additional difficulties result because the breast may move slightly or be slightly deformed between the earlier and later images. Even slight misalignment makes it difficult to determine whether the same lesion is comparable in earlier and later images. Even if positions, compressions and projection angle correspond well in before and after images, side-by-side comparison of complex tissue patterns is difficult, and slight changes in tissue may escape detection.

SUMMARY OF THE INVENTION

An image processing system and method visually documents historical changes in a medical image by processing and comparing historical with later images. A composite image is created which visually emphasizes the temporal differences between historical and later images. Preferably three-dimensional, digitized images, displayable in various projections, are stored for archival purposes on computer readable media.

To properly relate the historical and later images, an image processor preferably exploits an optical correlator to register the images accurately, by finding a transformation which produces a pre-determined degree of correlation between the images, then adjusting one image accordingly. The images are then compared, preferably volume element by volume element ("voxel by voxel"), to detect temporal differences between historical and later images. A composite image is displayed with synthetic colors or other visual clues to emphasize the scalars in the imaged tissue, based on temporal differences between the historical and later images.

BRIEF DESCRIPTION OF THE DRAWINGS

FIG. 2b is a flow diagram showing the continuation of the method of FIG. 2a;

FIG. 5a is a flow chart showing the initial steps of a method of registering earlier with later images, suitable for use in the registration step of FIG. 2a;

DETAILED DESCRIPTION OF THE INVENTION

Overview of Apparatus

Figure 1:
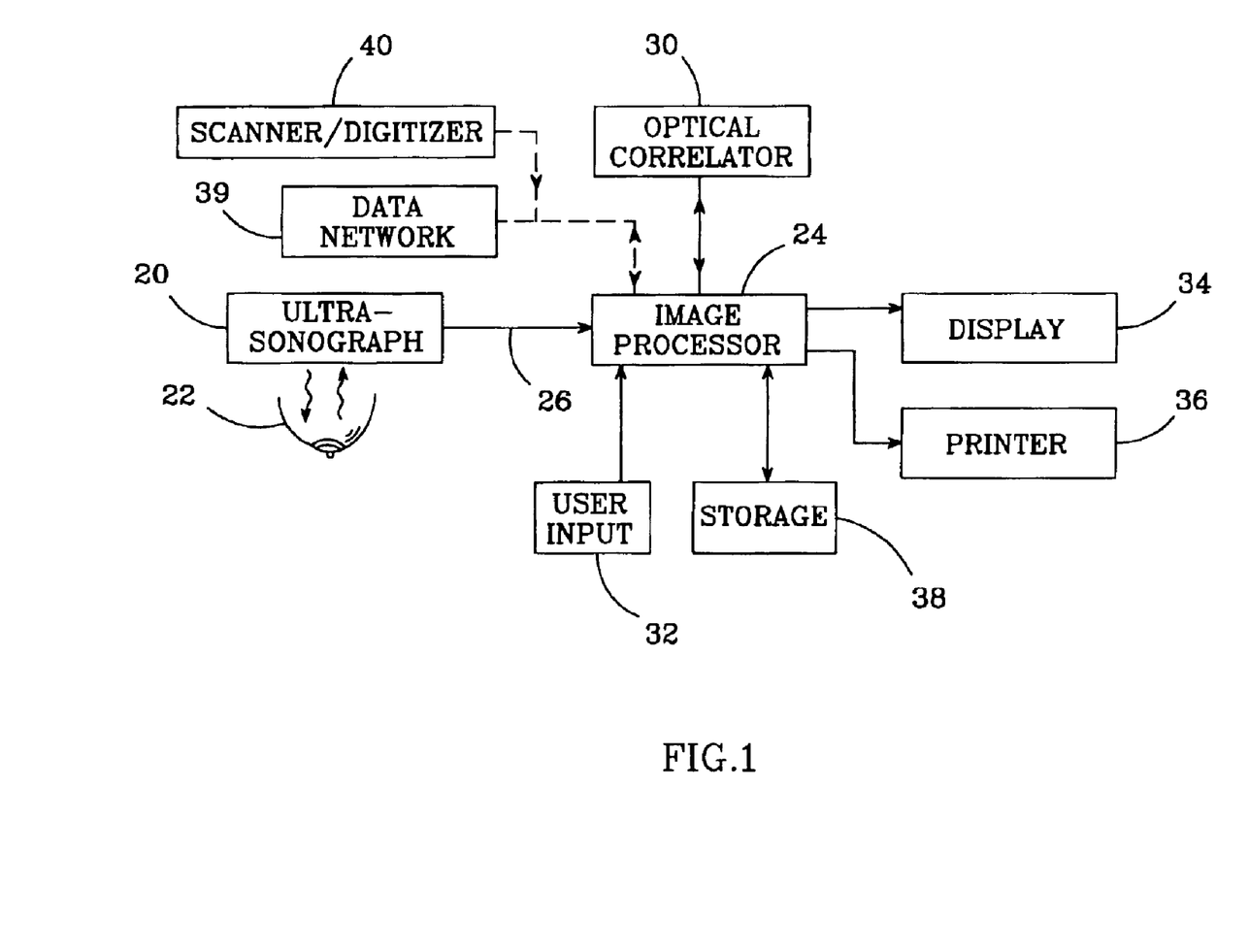
FIG. 1 is a system level block diagram of an apparatus in accordance with the invention.

FIG. 1 shows an apparatus in accordance with the invention and suitable for practicing its method. An ultrasonographic imaging system 20 (or its equivalent) images a patient's breast 22. The imaging system 20 provides digital image data to an image processor 24 via an input channel 26. An optical correlator 30 is preferably interfaced with and controlled by the image processor 24 to provide high-speed image processing (correlations) of pre-processed image data. A user input device 32 (typically a keyboard and/or graphical pointing device such as a mouse) is interfaced to the image processor 24 to allow user control of the image processor 24. Graphic output is displayed by the image processor 24 on a display 34, which is preferably a color-capable video display. A printer 36 is preferably also interfaced with image processor 24 to produce "hard copy" printouts which record the imagery, most preferably with multi-color, high resolution graphics. A storage device 38 such as a CD-ROM writer, digital tape storage, DVD, or similar digital storage device should preferably be also interfaced with the image processor 24 to record and store imagery in a digital data format, for archiving. Optionally, the image processor 24 could be also interfaced to a data network 39 to allow the exchange of data with distant users, or to access other sources of image data. Instead of or in addition to the data network, the image processor 24 can be interfaced with a digitizing scanner 40 which allows input of historical imagery such as X-ray mammograms.

The image processor 24 is preferably a 64 bit workstation such as the Silicon Graphics 02, although less powerful processors could be used at the expense of speed or resolution. The ultrasonographic imaging system 20 should preferably be capable of sweep scanning, to provide the multiple slices of imagery for assembly into a three-dimensional data set. Either a dedicated processor integral with the ultrasonographic imaging system 20 could provide such assembly, or it could alternatively be performed by-the image processor 24.

Overview of Method

Figure 2A:
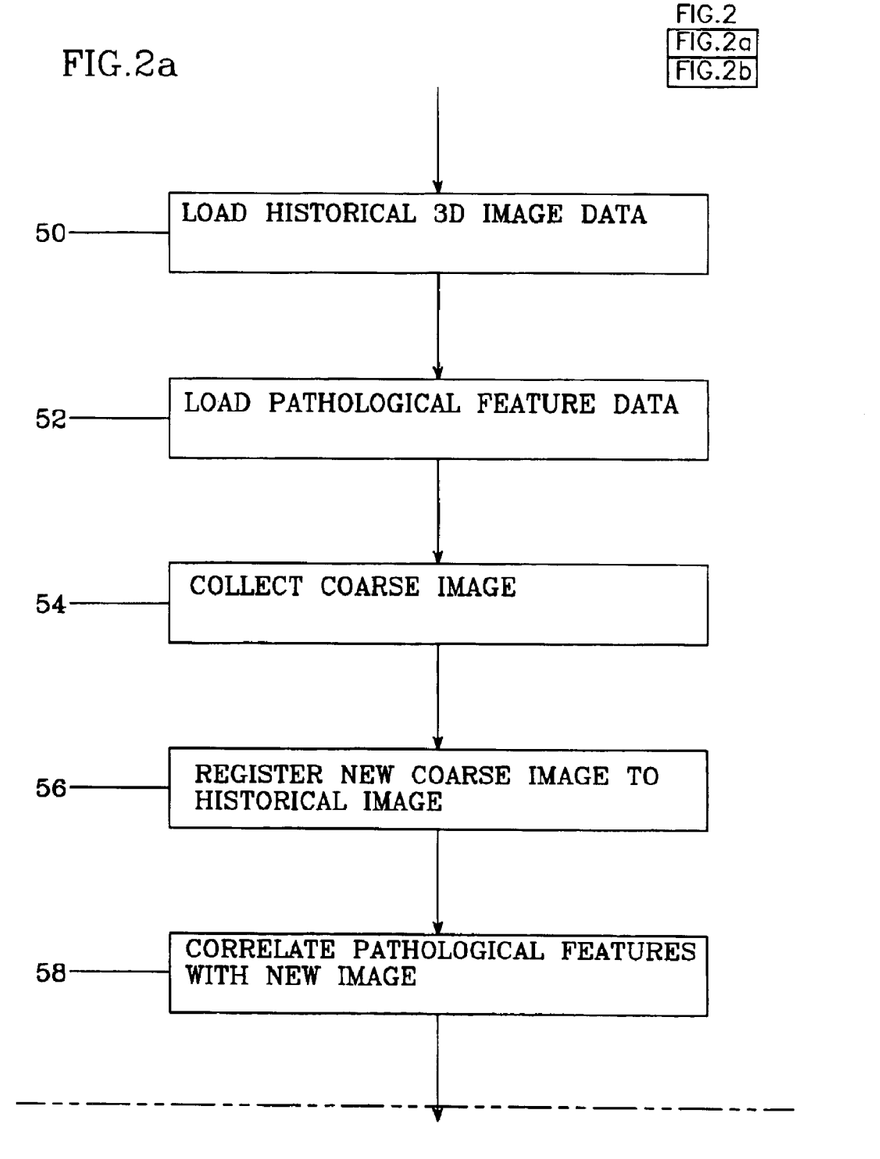
FIG. 2a is a summary level flow diagram of a method for comparing historical with more recent medical imagery in accordance with:the invention.
Figure 2B:
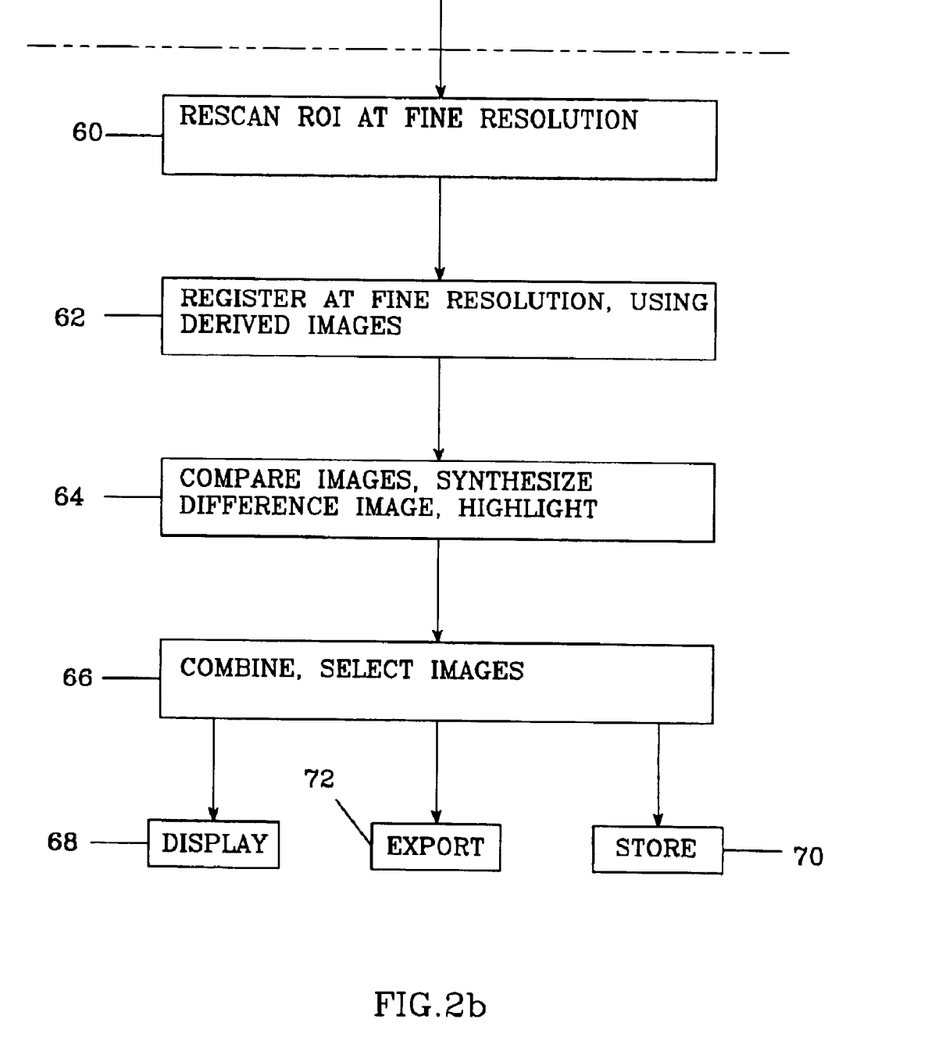

FIGS. 2a and 2b summarize a method used in accordance with the invention to compare historical with later mammographic images. First, the image processor 24 inputs (step 50) historical image data. Preferably the image data is available from a data network 39, but alternatively it could be obtained by scanning film imagery by digitizing scanner 40. If available, three dimensional historical image data is preferred. As another option, the historical data could be retrieved from a mass storage device 38 rather than loading by inputting the data.

Next, in step 52, pathological feature data is preferably loaded by the image processor 24 (preferably from a data network but alternatively by retrieval from storage or through another input channel). The pathological feature data is useful for narrowing the region of interest for image processing, and could be provided in any of several useful forms. Typically, a physical region of interest (ROI) in the historical image has been previously identified by a radiologist or other professional, and the coordinates of that region recorded in association with the historical image. In that case, the coordinates of the ROI are the pathological feature data. Alternatively, certain image shapes or characteristics, stored in a pathological image library, could be compared with the current image by image correlation to define the pathological region as described below in connection with FIGS. 6a–6c. A further alternative is to employ known automated methods for the detection of abnormalities in digital mammograms. For example, see U.S. Pat. No. 5,491,627 to Zhang et al. (1996). The locations of any detected suspect lesions, as determined by such an automated method, could be used as the pathological feature data to identify and locate the ROI in the image.

Next. (step 54) a coarse resolution, three-dimensional image sweep of the patient's breast is taken, preferably by sweeping an ultrasonic imaging head linearly across the breast thereby obtaining a plurality of image slices which collectively define a three-dimensional image. The resulting coarse image is stored (also in step 54). The coarse breast image of step 54 is then manipulated by the image processor to properly register it (step 56) with the historical imagery, to at least a preliminary degree of registration. This initial, coarse level of registration can be performed by processing only a very simplified image, to improve processing speed. For example, the image can be first compared pixel by pixel (or voxel by voxel) to a threshold value, and a binary product image produced based on the result at each pixel (voxel). In the threshold processed image, only the most obvious features, such as the breast outline and chest wall, will be recognizable. The images can then be rotated and shifted either manually (by operator command) or by the registration method described below in connection with FIGS. 5a and 5b, to crudely register the images. The initial registration of step 54 preferably operates on the whole image but at very low resolution: for example, the entire image is suitably mapped, after thresholding, onto a 256 by 256 matrix, then registered by the correlation method of FIGS. 5a and 5b. This suffices to approximately register the images, based n gross features only.

Next, to obtain improved registration between the historical and new image, the image processor correlates the pathological feature set with the new image (step 58), preferably by the method described below in connection with FIGS. 5a and 5b. The information gained from the correlation operations allows better registration of the new image with the historical imagery and defines an ROI in the new image. This approach to 'better' registration provides for improved temporal difference resolution, and makes the associate measures more accurate within the region of interest. The ROI thus defined is then re-scanned (step 60), preferably as described above, with scanning ultrasound equipment but with a finer level of resolution. Finer resolution can be obtained by using slower scan speeds, higher frequency ultrasound, finer and more numerous receive sensors, or other techniques as known in the art. The fine scan, being preferably thus restricted to the ROI, can be executed in a shorter time than would be required to image the entire breast at a fine level of resolution.

The image processor 24 next proceeds to register the new, finely resolved ROI image with the historical image of the corresponding ROI (step 62). This new registration step 62 is performed with finer resolution than the previous coarse registration (step 56), but preferably the operations are restricted to a smaller region of imagery, thus preserving a practical, limited computation time. This results in accurate and precise registration between the go historical and the new tissue ROIs. Preferably, both ROIs are three-dimensional volume regions which are aligned by registration in three dimensions.

After the historical and new images are aligned, they are compared in step 64 on a point-by-point basis, to obtain a temporal difference image which emphasizes the temporal changes which have occurred. For example, if digitized two dimensional images are considered, the images are preferably first normalized to a common average value, then corresponding pixels are subtracted and the temporal difference values stored in a corresponding position in a temporal difference image. Analogously, if three-dimensional imagery is available (which is greatly preferred), voxels at corresponding locations in the early and later images are subtracted one from the other, and the result stored in a voxel of a temporal difference (volume) image. (A "voxel" is a unit of graphic information that defines a small volume element in three-dimensional space. It is the three-dimensional analog of a "pixel" which defines an area element in two-dimensional space.) Thus, normalized before and after images can be subtractively compared, voxel-by-voxel, to obtain a three-dimensional temporal difference image which represents the temporal differences between the before and after images.

As a result of step 64, at least three images are available to the image processor 24: an early (historical) image; a current image; and a temporal difference image. These images are then combined and/or selected for display (step 66) in various ways, as directed by user input from input device 32. Finally, the resulting image or images are displayed (step 68) and preferably stored (step 70) and/or exported (step 72, preferably via the data network). It is highly preferable that the imagery be coded to emphasize temporal differences between the earlier and later images. For example, the temporal difference image can be coded in a distinct color for display based on correlation output values, then superimposed on the early image, the later image, or a composite. Various other conventional methods could be equivalently employed to visually emphasize temporal image differences. For example, in one variation the temporal difference image can be displayed in intermittent, flickering display superimposed on either of the historical or current images. Significantly, the invention easily detects temporal differences between the earlier and later images, visually displays the images, and visually emphasizes these temporal differences.

The product images from step 66 should preferably be recorded (step 72) for archival purposes, preferably on a high-density, long persistence medium such as magnetic tape memory or writable CD-ROM. Preferably a three-dimensional volume image should be stored, but to save storage space, operator selected projections can be derived (by programming the image processor 24 under control from the operator) and stored as two-dimensional imagery. Three dimensional imagery is preferred, despite its greater storage demands, because it can be more easily compared with other images (either previous history or subsequent development). The three-dimensional imagery can be digitally manipulated by rotation, scaling, translation then projected to provide comparison with any view; two dimensional imagery does not provide sufficient information to carry out the aforementioned manipulations without loss of information or introduction of ambiguities in the resulting image. The location of significant changes in the image should preferably be tagged with an identifier, to cross-link to a potential future tissue sample specimen number.

The method may be repeated to compare multiple historical images. Either one or multiple combined images can be stored for archival and to document historical developments.

Registration Method:

The success of the above described procedure depends in part upon the accuracy with which the earlier and later images are registered (in steps 56 and 62 of FIGS. 2a and 2b) before comparison. Slight movement or deformation of the breast tissue or the scanning apparatus is to be expected between the earlier and later scans. The movement may include translation, rotation about any axis, or slight compression or expansion (in addition to biological tissue changes). To adequately register the images in step 56 or 62, therefore, a computationally practical and fast method of registration is preferred. A preferred method of registration takes advantage of the specific computational abilities of an optical correlator (discussed in detail below in connection with FIG. 9). This preferred method (suitable for use in step 64 of FIG. 2b) is best described with reference to an example of a particular coordinate system, to aid in visualization.

Figure 3:
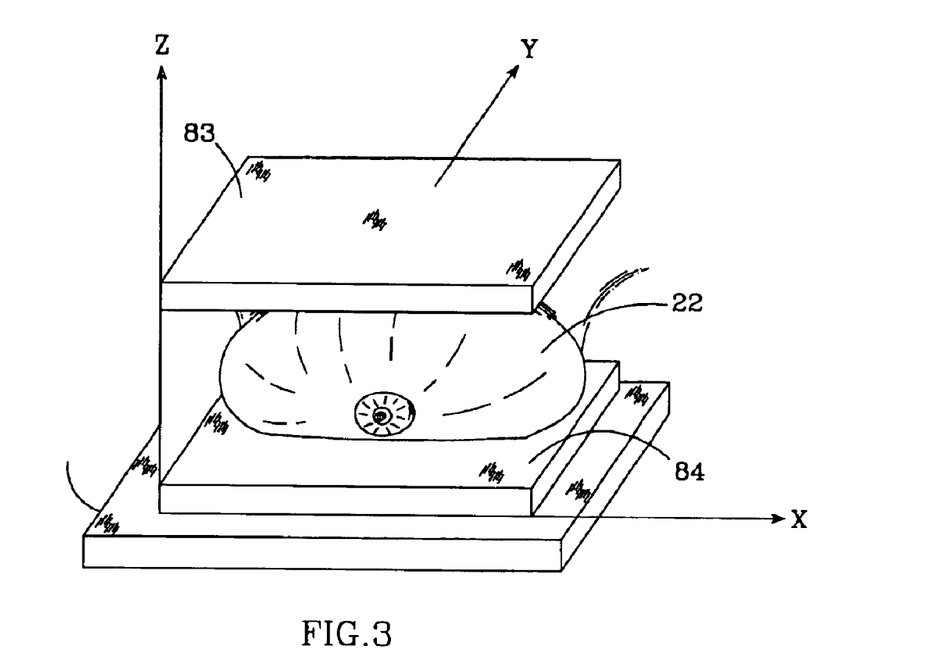
FIG. 3 is a perspective view of one geometric arrangement which can be used to obtain ultrasonographic imagery of a human breast for use by the invention.

FIG. 3 shows how a sonographic or radiographic breast image might be oriented with respect to a particular useful coordinate system. The system is conveniently illustrated in a Cartesian, rectilinear coordinate system having linear, perpendicular axes x, y and z, but the invention is not limited to such a coordinate system. The patient's breast 22 is scanned with ultrasound by the ultrasonic imaging system 20 (omitted for clarity, but shown in FIG. 1). With a patient preferably sitting facing the imaging system, the patient's breast 22 is preferably slightly compressed between pressure plates 83 (upper) and 84 (lower) in a manner that makes maximal use of prior information (such as x-ray images). In positioning the breast between the pressure plates, edges of the plates will contact the patient's chest above and below the breast. Because of slight movement between image acquisitions, the patient's breast in the imaging system, the axes of the later imagery do not in the general case exactly correspond with the x, y and z axes of the historical image, but may differ by a coordinate transformation: for example, they may differ by translation in the x, y or z directions, and by rotation about any axis. Rotation about the z axis is especially likely.

Figure 4:
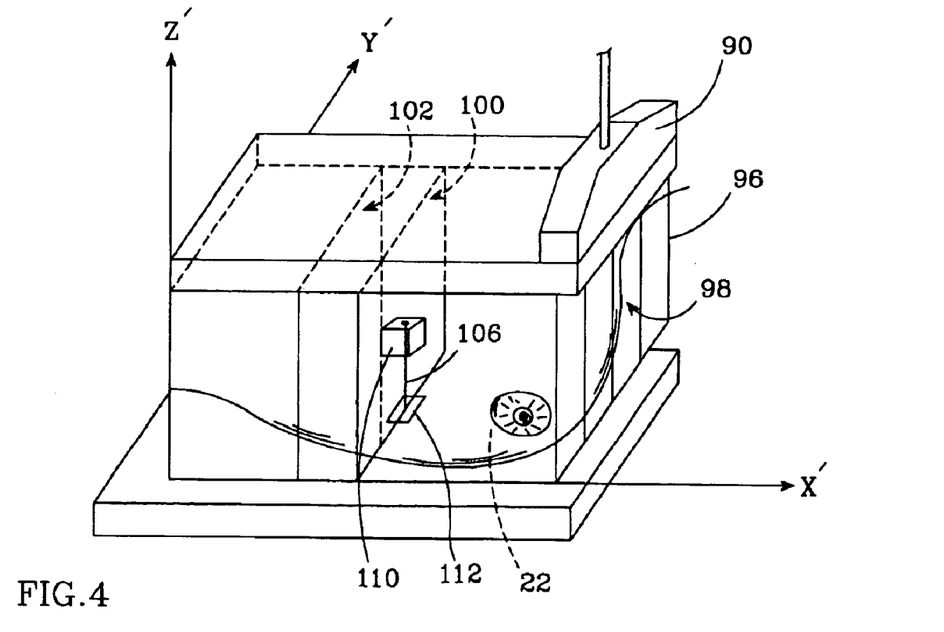
FIG. 4 is a perspective view of the arrangement of FIG. 3, showing further details of a scanning scheme for obtaining three-dimensional image data from a human breast.

With the breast 22 in position, ultrasonic scanning is preferably performed in planes (or surfaces), which will in general be non-parallel to that of the Y-Z plane in FIG. 3. FIG. 4 shows a typical geometry in which the scanhead 90 includes a linear array of ultrasonic transducers aligned parallel to the y axis. The scanhead 90 transmits ultrasonic pulses in the directions of the parallel lines 96, which are preferably perpendicular to the x'-y' plane and parallel to the z'-y' plane. The array of transducers in scanhead 90 probe the underlying tissue lying. (approximately) on lines 96 by detecting returns of the ultrasonic pulses caused by acoustic impedance discontinuities or reflecting surfaces within the tissue. The delay time between transmitting a pulse and receiving an return is indicative of the depth of the discontinuity or surface which caused the return. A characteristic such as magnitude, phase, or frequency of the returns is digitized and is plotted against the depth (z' axis) information and the information from the multiple transducers (dispersed in the y' direction) is assembled to construct an array representing a cross-sectional view of the tissue in a slice 98 parallel to the y'-z' plane and lying under scanhead 90.

Multiple slices can be scanned either by providing multiple scanheads, a two-dimensional scanhead array, or by moving the scanhead across the breast, for example in the x' direction in FIG. 4. The planes of only a few of the multiple slices, specifically slices 98, 100, and 102, are shown. In practice a large number of slices is desirable, for better resolution. A complete set of such slices is preferably scanned to form a three dimensional information set for at least some region of interest (ROI) chosen from the breast, which is preferably stored in a data structure (such as a three-dimensional array) to represent a three-dimensional image.

Ultrasonographic equipment is available commercially which can be used as the ultrasonographic imaging system 20 described above. A two-dimensional array of ultrasonographic data is usable by the invention, but with a diminished amount of useful information in the resulting display.

Keeping in mind the exemplary coordinate system of FIG. 3, a method suitable for registering the historical and later images (step 64) is shown in the flow chart of FIG. 5a (and continued on FIG. 5b). By this procedure the image processor 24 determines the proper coordinate transformations of scale, position, and rotation which will align the historical and later images. The image processor 24 accesses (step 102) the stored ultrasound images from ultrasonographic imaging system 20 and extracts (step 104) a two-dimensional representation preferably by projecting or "collapsing" the three-dimensional ultrasound data onto a single plane. One method of doing this is by "cumulative projection": a projection of the three-dimensional data set onto a two-dimensional plane by summing the data entries along vectors which are perpendicular to the projection plane. One such vector, vector 106, is indicated on FIG. 4 for illustration. The density values associated with the voxels (three dimensional discrete volume cells) such as voxel 110 are summed along the vector 106. The summation of those density values yields a scalar value which indicates the sum of the tissue densities along that vector. This scalar value is associated with the pixel 112 at the intersection of the vector 106 with the x'-y' plane. Repeating this summation for multiple parallel vectors results in a set of values which defines the projection of the three-dimensional sonographic imagery onto the x'-y' plane. This projection is preferably applied to both the historical and later imagery. Thus, returning to FIG. 5a, both three-dimensional data sets are projected onto is respective two-dimensional images and stored (step 114).

The purpose of collapsing the three-dimensional images into two dimensions is to facilitate correlation, which is preferably accomplished by use of an optical correlator. Such correlators conventionally require two-dimensional imagery as correlation inputs. In some applications, the historical imagery will already be in two-dimensional projection, having been previously selected and projected to adequately visualize the lesion(s) of interest. In such a case only the later imagery must be collapsed.

As an alternative to collapsing the images by simple projection, as described above, a three-dimensional image can be processed to create a "discriminate filter." Such filters are known and facilitate registration by providing a correlation filter which a composite of many images which differ by rotation about an axis. This allows testing of multiple, rotated slices simultaneously, by correlation with a composite discriminate filter. Once a discriminate filter is determined with acceptable correlation (at least equal to a predefined level of correlation) an individual filter is then selected from the set of slices which was used to compose the composite. In some cases, this method can greatly accelerate the search for best correlation.

The projected images are optionally further pre-processed (step 116). Pre-processing 116 can include any of a variety of known image processing techniques including (without limitation) contrast modification, smoothing, geometric transformation, thresholding or the selection of a region of interest. Depending on the type of optical correlator 30 used, as discussed in detail below, this step may also include two-dimensional Fourier transformation of the digitized x-ray image to prepare it for subsequent optical correlation in a Vanderlugt optical correlator.

Next the image processor 24 adjusts (step 118) the relative scale of the two images so that they better correspond in scale. This can be done by various methods. For example, one method is to match the total area of the cross section of the breast area between the outer outline and the chest wall in both images. In this method, the images should preferably first be processed to remove low contrast features, leaving only the easily visible outline of the breast and the chest wall. The area between these features in the two dimensional images is then measured, for example by numerical integration by the image processor 24. The area should correspond in both images. If the areas do not correspond, it is possible that the degree of compression has changed, which can compress or expand the breast. A scaling correction factor is then preferably applied in step 118 to correct as closely as possible. On the other hand, it is possible in many cases to maintain a relatively constant compression. In such cases, little or no re-scaling is necessary.

Figure 5A:
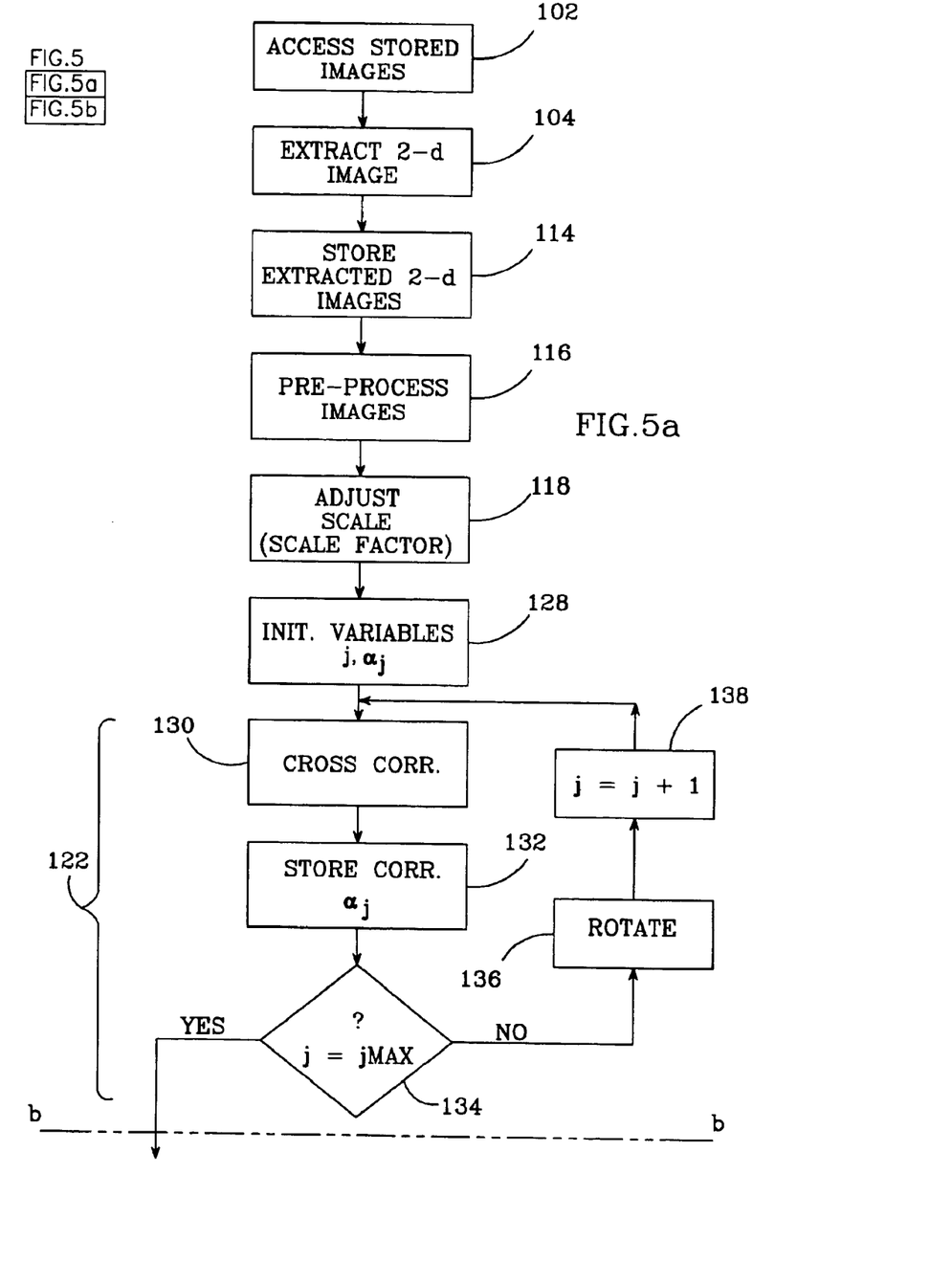

After scale correction; the image processor 24 determines the rotation and translation necessary to align the images, preferably by interactively performing the steps grouped within the instruction loop 122 in FIG. 5a. First, two variables are initialized (step 128): a counter j to control execution of an instruction loop, and an associated rotation angle $\alpha_j$. Next, a cross-correlation of the dual images is computed (step 130). Preferably this step is accomplished by using the optical correlator 30 to perform the actual correlation computation, under control of the image processor 24. (The details of the optical correlator are discussed below, in connection with FIGS. 5 and 6) The cross-correlation (step 130) produces a two-dimensional correlation output image indicating the degree of image cross-correlation, which is stored (step 132) along with the associated rotation angle $\alpha_j$. The image processor then checks (step 134) the counter variable to discover whether it has completed a prescribed number of iterations of the instruction loop 122.

Next, if the counter variable j has not reached jmax, the image processor 24 continues and rotates (step 136) one of the dual images relative to the other by some angular increment, for example by rotating the historical image one degree about an axis centered in the frame and parallel to the z axis. The counter is incremented (step 138) and the procedure loops back to step 130 to perform another cross-correlation, this time with the images rotated incrementally. The procedure is repeated until some number (jmax) of differently rotated correlations has been performed. The parameter jmax should be chosen to be large enough so that the range of the associated angle $\alpha_j$ encompasses the anticipated maximum possible range of rotation. For breast examination in the geometry shown in FIGS. 3 and 4, a range of less than 10 degrees is adequate in most cases.

The rotations applied in step 136 are not limited to rotations about a single axis, but can include rotations about multiple independent axes (or, equivalently rotations about an axis obliquely oriented with respect to the orthogonal axes shown). This allows the correction for an oblique viewing angle of one image with respect to the viewing angle of the other.

After the counter j reaches jmax the image processor 24 exits the instruction loop 122. The procedure continues as diagramed in FIG. 5b. The correlation output images previously stored in the various iterations of step 132 are compared (step 140) with one another to find the correlation output image with the maximum correlation, and its associated angle of rotation $\alpha_j$. The value $\alpha_m$ (the rotation angle which produced maximum correlation) is stored (step 142) and either the historical or the later image is rotated (step 144) by $\alpha_m$ to bring it into the same orientation as its counterpart.

Figure 6A:
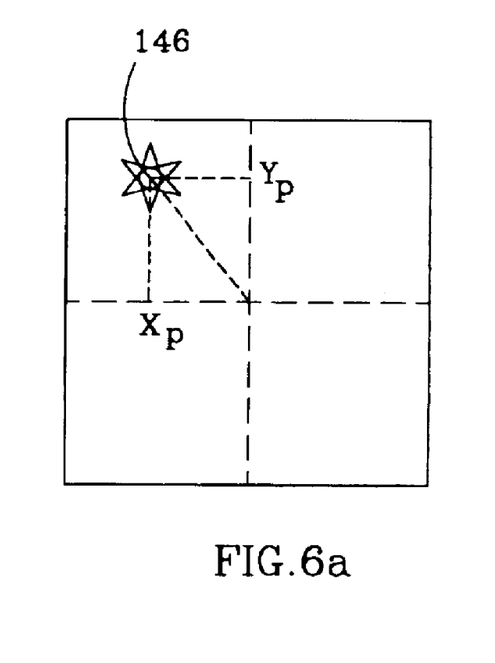
FIGS. 6a, 6b, and 6c, show simplified examples of an input image, a filter template, and a resulting correlation output image, respectively, in an example of a suitable cross-correlation operation which discovers positional offset of correlated images in the method of FIGS. 5a and 5b.
Figure 6B:
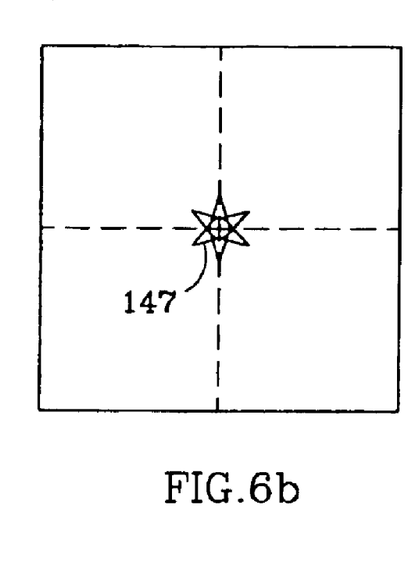
Figure 6C:
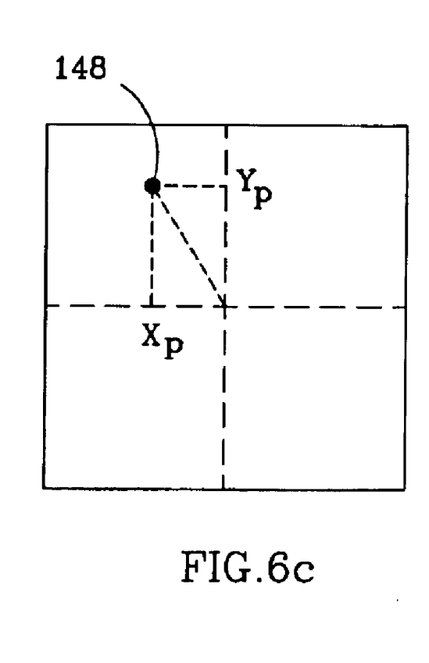

It should be understood that in addition to discovering the correct scale and rotation angles, the cross-correlation (step 130) in the above described procedure produces an output image which reveals the correct translation (position shift) which best aligns the dual images. The translation information is contained in the result of the cross-correlation operation (preferably in two-dimensions) defined as:

$$H(x,y)=g(x,y)*f(x,y)=\int\int f(\alpha,\beta)g(x-\alpha,y-\beta)d\alpha d\beta \qquad (1)$$

Where f and g are functions of two variables (images), x and y are the spatial variables of the two-dimensional images, $\alpha$, and $\beta$ are dummy variables of integration, H is the cross-correlation of functions f and g, and the range of integration is across the entire image. If f and g differ only by a positional offset in x and y, H(x,y) will have a sharp peak at a position $x_p$, $y_p$ which is displaced from a central, correlation alignment position (typically defined as x=0, y=0) by a displacement corresponding to the offset between f and g. This well known result has been used to recognize and locate features of initially unknown locations in a field by reference to a template. See, for example, Russ, John C., *The Image Processing Handbook* (CRC Press, 1992), pp. 218–24. A simplified example is shown in FIGS. 6a–6c. The input image, a star 146 at an offset position shown in FIG. 6a, is correlated with a filter derived from the centered star-shaped template 147 shown in FIG. 6b. The resulting correlation output shown in FIG. 6c has a peak 148 at a position $x_p$, $y_p$ corresponding to the offset between the input image and the filter template. To align the images with a correlation peak at position $x_p$, $y_p$ it is sufficient merely to translate one of the images by a displacement equal to the offset $x_p$, $y_p$.

Returning to FIG. 5b, the image processor 24 next analyzes (step 154) the correlation output image to locate the positional offset of the correlation peak from an aligned correlation position, then translates (step 156) one image relative to the other as necessary to better align the images. After finding the optimal combination of rotations, scalings and translations to align the earlier and later images, the image processor 24 preferably stores (step 158) the transformed images and the transformation parameters in its associated memory and preferably outputs (step 160) the transformed images to a display device 34.

Figure 7:
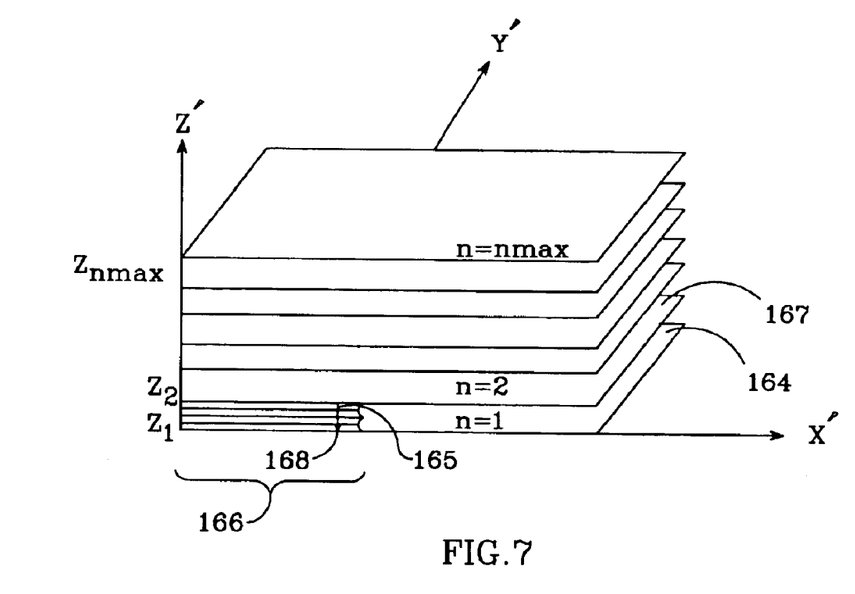
FIG. 7 is a perspective view of an arrangement of planar slices of a breast which can be selected for image processing of three-dimensional breast images by the invention.

In one embodiment the invention utilizes additional three-dimensional information about the subject body by further correlating the images in order to align the z direction (depth). To accomplish this, the ultrasonographic imagery is first partitioned by image processor 24 into conveniently defined slices, for example slice 164 as shown in FIG. 7. Each slice includes one or more layers of the three dimensional ultrasonographic image data. The slices are defined and calculated by image processor 24, for example by summing data points along vertical vectors such as 165, to collapse multiple thin layers into a thicker slice (a "partial cumulative projection"). In FIG. 7, for example, multiple thin layers 166 of ultrasonographic imagery (shown only partially to clarify FIG. 7) might lie between bottom slice 164 and the immediately overlying slice 167. The partial cumulative projection is taken point-by-point, by summing the ultrasonographic image values at points along vectors such as vector 165, and accumulating the result to the point 168 where vector 165 intersects the slice 164. The accumulated data values at each defined point on slice 164 collectively define the slice.

In a typical application, slices with thickness of 5 millimeters or less are suitable. Although planar slices are convenient for purposes of illustration, in some applications the slices might usefully be taken along non-planar contours. Such slices are also within the scope of the invention. Thinner slices are desirable for better depth definition with thin features.

To best align the earlier and later images, corresponding slices in each are individually correlated to find their best registration, for example by the method described above. In one variation of this technique, the slices are defined parallel to the X'Y' plane. In another variation, the slices are defined in another plane (the slice under the scanhead, parallel to the Z'Y' plane, for example) and registered by the above described method, then reassembled. By registering each slice, the three-dimensional imagery can be aligned to account for variations in shear or torque between the earlier and later image acquisitions, as might be caused by variable deformation of the breast under varying pressure.

Figure 5B:
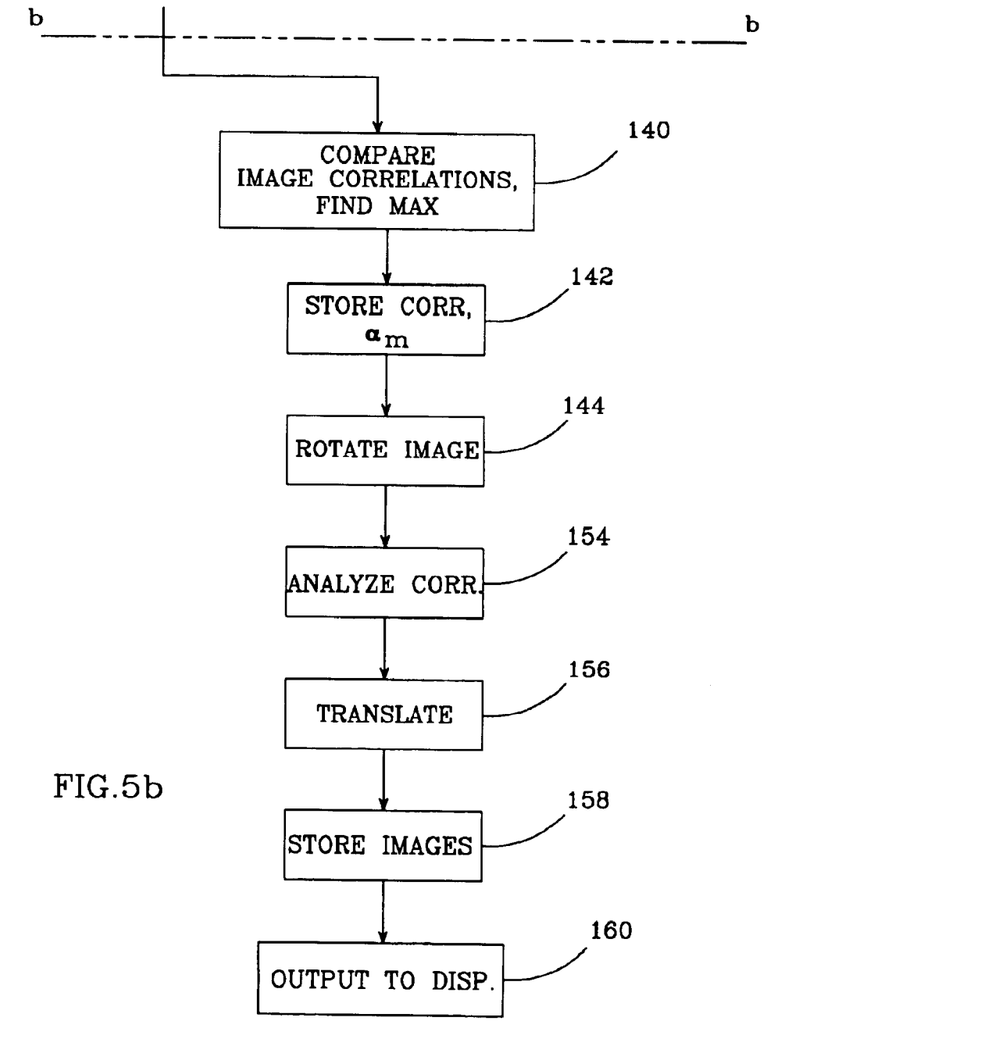
FIG. 5b is a flow chart continuing from FIG. 5a, showing the further steps in the registration method.

The fine registration step of step 62 (in FIG. 2) is preferably performed by essentially the same method as the coarse procedure: i.e., the method of FIGS. 5a and 5b. The fine registration will yield correlation results which rely upon finer features than the coarse registration. Small constellations of microcalcifications, in distinctive patterns, will yield correlation results which allow registration of the ROIs at a very fine scale. However, perfect correlation will not be obtained in general, particularly if tissue changes have occurred between the earlier and later images. Nevertheless, detection of optimum correlation should permit satisfactory registration. In those cases in which a dramatic tumor growth has occurred, the tissue changes will be more dramatically visually conspicuous, even with imperfect registration; contrariwise, if only slight tissue changes have occurred, good correlations will be obtainable, resulting in precise alignment.

Figure 8:
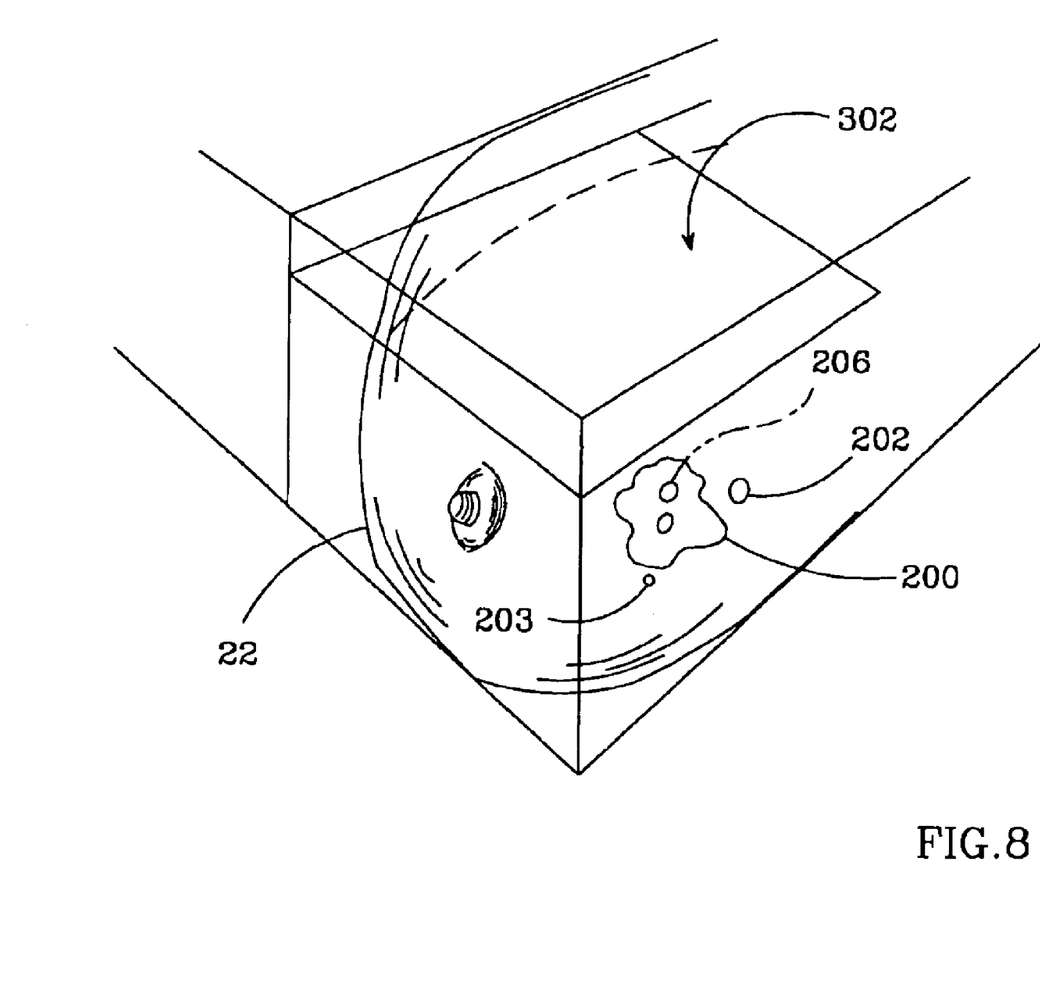
FIG. 8 is a perspective diagram representing a typical visual display of a composite image created by the invention to document historical changes in breast tissue.

After the earlier and later ROI images are adjusted to best register them, they can be either combined by adding, voxel-by-voxel, or compared by subtracting, voxel-by-voxel. Temporal differences between the images are easily highlighted by changing the color at voxels which show high variation between the dual images. FIG. 8 shows an example of one typical display of a combined image (in this case, a composite of earlier and later images, with temporal differences highlighted). The outline of the breast 22 is shown, with highlighted suspected lesion 200 (simplified for illustration) as revealed by a recent ultrasonogram. Other more static regions of density 202 and 203 are shown, which would suitably be displayed in a neutral color or grey scale. The earlier lesion region 206 is surrounded by the later, larger lesion 200. Suitably the later region 200 would be highlighted, by example by display in a conspicuous color such as pink. The smaller lesion 206 (visible in the earlier historical image) would preferably be coded in a different color (for example, green). This three dimensional image, easily digitized and archived on computer readable media, provides easily readable documentation of the historical image changes, and can be retrieved for evidence of tissue changes. The image processor can also extract slices such as that cut by imaginary plane 302, and display the slice as a two-dimensional section for detailed inspection. Preferably, the processor is programmed to respond to user input so that any slice can be selected for display, or the user can sweep through multiple slices to view details of interest.

In the procedures depicted in FIGS. 5a and 5b it is highly preferable that the correlation operations be carried out by an optical correlator. In the preferred embodiment, the image processor 24 electronically writes the dual images to the optical correlator 30. The optical correlator 30 preferably performs the correlation operations and returns a resulting correlation image to the image processor 24.

Optical correlators use wave optics to correlate images in two dimensions by first performing essentially a two-dimensional spatial Fourier transform on a two-dimensional source image. This method takes advantage of a well known mathematical property of the Fourier transform: many operations including correlation are more easily calculated in the Fourier transform domain than in the original spatial domain. Specifically, a two-dimensional correlation operation is defined by equation 1 (above), where $f(x,y)$ and $g(x,y)$ are the two-dimensional functions or images to be cross-correlated, and $\alpha$ and $\beta$ are dummy variables of integration. This operation can be performed digitally for each point x,y by numerical techniques, but a very large number of calculations are required even for one image correlation. Performing such an operation digitally is very time consuming and requires inconvenient lengths of time on any but the fastest digital computers.

Unlike a conventional digital computer, an optical correlator can very rapidly perform a correlation operation, correlating a source image with a filter image by (1) optically Fourier transforming a source image, (2) comparing the source and filter image in the Fourier transform domain, and then (3) performing an inverse Fourier transformation to produce the correlation pattern in a spatial representation. An optical correlator can accomplish these operations much faster that a digital computer because the optical Fourier transformation is executed as a simultaneous operation on all points of the source image, using inherent properties of wave optics to generate the Fourier transform in two dimensions. The speed of the device is limited for practical purposes only by the available read and write speed of the data transfer to the correlator; the actual optical processes occur in fractions of a nanosecond in typical optical correlators.

The principles of the optical correlator are known, and have been described for example in the U.S. Pat. No. 5,311,359, to Lucas et al. Compact optical correlators suitable for use in the present invention are commercially available from Litton Data Systems, Inc., in Agoura Hills, Calif., as well as from other sources. Alternate types of optical correlators such as the Joint Transform Correlators described in U.S. Pat. No. 5,650,855 to Kirsch et al., U.S. Pat. No. 5,216,541 to Taksue et al. or U.S. Pat. No. 5,438,632 to Horner, may also be employed with the invention.

Figure 9:
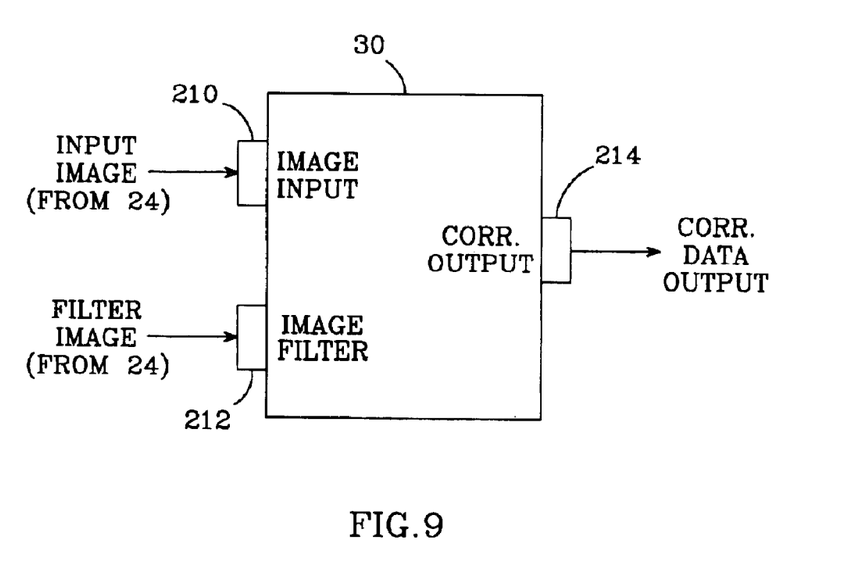
FIG. 9 is a symbolic diagram of an optical correlator, optionally used in accordance with a variation of the invention for rapidly performing two-dimensional correlation operations, thereby aiding in registering the historical and later images.

For purposes of describing the present invention, the optical correlator 30 may be considered functionally as an electro-optical device having three (electronic) ports, as shown in FIG. 9. The three ports include: (1) an image input port 210 for receiving an electronic signal encoding an input image for correlation; (2) a filter input port 212 for receiving a second electronic signal encoding a second image or "filter" for correlation; and (3) an output port 214, typically from a charge coupled device (CCD) imager, which converts the correlation image into electrical form for output. In addition the device requires a source (not shown) of preferably coherent electromagnetic radiation, typically a laser, which provides the medium used for computation.

Both the image input port 210 and the filter input port 212 are realized as two-dimensional spatial light modulators (SLMs) organized as two-dimensional image matrices, with addressable image pixels (typically arranged in the familiar row and column pattern). Accordingly, the input image must be formatted (suitably by image processor 24) to fit the matrix; and each pixel of data should preferably be addressed, under control of the image processor 24, to the spatially corresponding pixel on the SLM. For example, in one embodiment of the invention, the image input port and the filter input port are realized as 256×256 pixilated matrices. Accordingly, in this embodiment the image processor 24, as part of pre-processing step 116 (in FIG. 5a), maps an ultrasonographic image onto a 256×256 matrix for output to the optical correlator 30. In a typical embodiment of the invention a Vanderlugt type optical correlator is used. In such a correlator the "filter" image must be pre-processed by two-dimensional Fourier transformation. In such an embodiment the image written to the filter port is preferably Fourier transformed by image processor 24 (for example in pre-processing step 116), to provide a frequency domain pattern. In an alternate embodiment, a joint transform correlator may be used as optical correlator 30. This eliminates the need for the digital Fourier transformation of the filter image, as the transformation is optically performed by the joint transform correlator.

Note that in conventional, practical high speed optical correlators, the SLMs and the photodetector matrix consist of discrete pixels rather than a continuously modulatable surface. Thus, the Fourier transformation and correlation operations can only approximate the discrete cross-correlation (given by equation 1, above). However, the approximation obtained is sufficient for image processing for most applications.

When the input the filter images have been written to the input and filter ports 210 and 212, the optical correlator produces an output image which is a two dimensional output correlation pattern having an optical peak or peaks (bright spot) at the position of greatest correlation between the collapsed sonographic image and the radiographic image. The degree of correlation is indicated by the intensity of the output signal. The position of the output peak on the two-dimensional matrix of the correlator output CCD indicates the translations or shifts of the images relative to one another. The output image is read from the output photodetector (CCD) 214 by the image processor 24 in the conventional manner, typically by shifting the CCD voltage values out sequentially in rows (or columns) and then digitizing, the output levels. The peak amplitudes of the 2D array provide the extent of correlation (degree of correlation) between the images. This scalar information is a measure of the temporal difference, and can be used as a measure of knowledge between images and supports actions that lead to a successful treatment or evaluation.

In many applications in which two images are to be correlated, it is irrelevant which image provides the filter and which the corresponding input image, provided that the filter image is presented (in a Vanderlugt type correlator) in a Fourier transform representation. However, in some particular embodiments it may be preferable to route the historical imagery to the input port 210 rather than the filter port 212. For example, if discriminate filters are derived from the later ultrasound imagery and are to be correlated, these filters would usually be derived in a Frequency domain representation and would thus more appropriately routed to the Filter port 212. On the other hand, if a search for a correlation is to be done with a brute-force, match search, then the multiple projections derived from the later imagery should be applied to the input port 210 (thus avoiding the need to perform numerous two-dimensional Fourier transformations).

Although the invention is described in terms of linear transformations of the coordinates, such as translation, rotation, and scale multiplication, the invention is not limited to linear transformations. Non-linear transformations of coordinate systems may be useful in some applications. . For example, the ultrasonographic information may be obtained with the breast differently deformed, as by a change of position of the subject, or by instrument pressure. By applying a mathematical transformation, which may in general be non-linear, a better mapping of the deformed subject breast onto the original subject breast can be obtained. Similarly, some scanning techniques may involve curvilinear, non-cartesian coordinate Systems which would be treated with non-linear transformations.

While illustrative embodiments of the invention are described above, it will be evident to one skilled in the art that numerous variations, modifications and additional embodiments may be made without departing from the invention. For example, the construction of the ultrasound imaging system or the geometries and coordinate systems employed may be varied. Various means of data storage, transmission, or processing may be employed. The resolution or type of image that is sent from the image processor to the optical correlator could also be altered. Three-dimensional cross-correlations are also possible (but computationally complex). To the extent that such operations can be decomposed into multiple planar operations, the use of the optical correlator as described above could greatly accelerate computations. Accordingly, it is intended that the invention be limited only in terms of the appended claims.

We claim:

1. A method of visually documenting historical changes in biological tissue, comprising the steps of:
   (a) obtaining a first image of a region of tissue;
   (b) obtaining pathological feature data for said region of tissue;
   (c) obtaining a second image of said region of tissue using a first level of resolution;
   (d) digitally storing said first and second images as digitized first and second images;
   (e) spatially adjusting at least one of said first and second digitized images to spatially register said images so that corresponding features in both images are mapped to corresponding positions, said spatially adjusting comprising:
      determining a coordinate transformation which produces at least a pre-determined degree of correlation between said first and second digitized images, and
      applying said coordinate transformation to at least one of said first and second digitized images, to align said images;
      said coordinate transformation determined by:
         applying coordinate transformations of scale, position and rotation to one of said first and second digitized images, to obtain a plurality of corresponding adjusted images,
         cross-correlating said adjusted images with one of said first and second digitized images, to produce a correlation output, and
         selecting a coordinate transformation which produces at least a defined correlation output from its corresponding adjusted image;
         said cross-correlating comprising:
            inputting said first and second images to an optical correlator, and
            reading said correlation output from an output of said optical correlator;
   (f) correlating said pathological feature data with said second image to define a historical region-of-interest (ROI) in said second image;
   (g) rescanning the defined ROI using a second level of resolution higher than said first level of resolution to obtain a third image;
   (h) spatially adjusting at least one of said historical and rescanned ROI images to spatially register said ROI images so that corresponding features in both images are mapped to corresponding positions; and
   (i) creating from said historical and rescanned ROI images a composite image which visually emphasizes temporal differences between said ROI images, thereby visually emphasizing historical changes between said historical and rescanned ROI images.

2. The method of claim 1, further comprising the step of recording said composite image for archiving.

3. The method of claim 2, wherein said step of recording comprises storing said composite image on a computer readable medium.

4. The method of claim 2, wherein said step of recording comprises printing an image based upon said composite image.

5. The method of claim 1, wherein at least one of said historical and rescanned ROI images is a three-dimensional image.

6. The method of claim 1, wherein said step of creating a composite image comprises:
   comparing an image intensity at a location in said historical ROI image with a respective intensity at a corresponding location in said rescanned ROI image, and
   determining a temporal difference image value based upon the temporal difference between said image intensity at said location in said historical ROI image and the respective intensity at said corresponding location in said rescanned ROI image.

7. The method of claim 1, wherein said composite image visually emphasizes temporal image differences by representing various regions of said composite image in synthetic colors, based upon temporal image differences between the historical and rescanned ROI images.

8. The method of claim 1, wherein said pathological feature data corresponds to predetermined image shapes or characteristics retrieved from a pathological image library.

9. The method of claim 1, wherein said pathological feature data is obtained by automated analysis of said first image.

10. The method of claim 1, wherein said second image is obtained using ultrasonic imaging.

11. The method of claim 1, wherein both of said historical and rescanned ROIs are three-dimensional volume regions which are aligned by registration in three dimensions.

12. A system for enhancing imagery of bodily tissues by relating earlier and later images, comprising:
   an image processor, programmed to:
      (a) receive a first image of a region of tissue;
      (b) obtain pathological feature data for said region of tissue;
      (c) obtain a second image of said region of tissue using a first level of resolution;
      (d) register the first and second images by controlling an optical correlator to find a position of correlation between said first and second images, said registering of said first and second images comprising:
         determining a coordinate transformation which produces a pre-determined degree of correlation between said first and second images, said coordinate transformation determined by:
            applying coordinate transformations of scale, position and rotation to one of said first and second images to obtain a plurality of corresponding adjusted images,
            cross-correlating said adjusted images with one of said first and second images to produce a correlation output, said cross-correlating comprising inputting said first and second images to said optical correlator and reading said correlation output from an output of said optical correlator;
            selecting a coordinate transformation which produces a defined correlation output from its corresponding adjusted image, and
         applying said coordinate transformation to at least one of said first and second images, to align said images;
      (e) correlate said pathological feature data with said second image to define a historical region-of-interest (ROI) in said second image;
      (f) rescan the defined ROI using a second level of resolution higher than said first level of resolution to obtain a third image;
      (g) register said historical and rescanned ROI images by controlling an optical correlator to find a position of correlation between said historical and rescanned ROI images;
      (h) derive a composite image from the historical and rescanned ROI images;

(i) compute temporal differences between said historical and rescanned ROI images; and
(j) emphasize said temporal differences in said composite image; and an optical correlator coupled to said image processor and arranged to perform said correlations.

13. The system of claim 12, further comprising a visual display, coupled to said image processor and receiving from said image processor said composite image, to permit a user to view said composite image.

14. The system of claim 12, further comprising an ultrasonographic imaging system, arranged to communicate ultrasonographic image data to said image processor to provide at least one of said first and second images.

* * * * *